United States Patent [19]

Hammon et al.

[11] Patent Number: 5,231,226
[45] Date of Patent: Jul. 27, 1993

[54] CATALYTIC GAS-PHASE OXIDATION OF METHACROLEIN TO METHACRYLIC ACID

[75] Inventors: Ulrich Hammon, Mannheim; Klaus Herzog, Ludwigshafen; Hans-Peter Neumann, Mannheim, all of Fed. Rep. of Germany

[73] Assignee: BASF Aktiengesellschaft, Ludwigshafen, Fed. Rep. of Germany

[21] Appl. No.: 948,425

[22] Filed: Sep. 22, 1992

[30] Foreign Application Priority Data

Oct. 1, 1991 [DE] Fed. Rep. of Germany ....... 4132684

[51] Int. Cl.$^5$ .............................................. C07C 51/25
[52] U.S. Cl. ..................................... 562/534; 562/532; 562/535
[58] Field of Search ..................... 562/532, 534, 535; 556/28

[56] References Cited

U.S. PATENT DOCUMENTS

| | | | |
|---|---|---|---|
| 4,564,703 | 1/1986 | Yamamoto et al. | 562/534 |
| 4,618,709 | 10/1986 | Sada et al. | 562/532 |
| 4,873,368 | 10/1989 | Kadowaki et al. | 562/532 |
| 4,925,981 | 5/1990 | Shimizu et al. | 562/532 |
| 5,155,262 | 10/1992 | Etzkorn et al. | 562/532 |

FOREIGN PATENT DOCUMENTS 2251364 5/1973 Fed. Rep. of Germany .
1390525 4/1975 United Kingdom .

*Primary Examiner*—Arthur C. Prescott
*Attorney, Agent, or Firm*—Oblon, Spivak, McClelland, Maier & Neustadt

[57] ABSTRACT

A process for the catalytic gas-phase oxidation of methacrolein to methacrylic acid in a fixed-bed reactor with contacting tubes, at elevated temperature on catalytically active oxides with a conversion of methacrolein for a single pass of from 40 to 95 mol%, wherein the reaction temperature in the flow direction along the contacting tubes in a first reaction zone from entry of the starting reaction gases containing the reactants into the contacting tubes is from 280 to 340° C. until a methacrolein conversion of from 20 to 40% is reached, and the reaction temperature is subsequently reduced by a total of from 5° to 40° C., abruptly or successively in steps or continuously along the contacting tubes until a methacrolein conversion of from 45 to 95% has been reached, with the proviso that the reaction temperature in this second reaction zone is not lower than 260° C.

4 Claims, No Drawings

CATALYTIC GAS-PHASE OXIDATION OF METHACROLEIN TO METHACRYLIC ACID

The present invention relates to a novel process for the catalytic gas-phase oxidation of methacrolein to methacrylic acid in a fixed-bed reactor with contacting tubes, at elevated temperature on catalytically active oxides with a conversion of methacrolein for a single pass of from 40 to 95 mol%.

Both methacrylic acid itself and esters thereof with lower alcohols are suitable as the starting monomer for the preparation of polymers for a wide variety of applications (for example adhesives).

The preparation of methacrylic acid by the catalytic gas-phase oxidation of methacrolein is highly exothermic. It is therefore necessary, as a consequence of a large number of possible parallel or subsequent reactions, to control the reaction temperature in order to obtain a highly selective conversion of methacrolein to methacrylic acid.

DE-A 2 251 364 discloses, for methacrolein conversions for a single pass of from less than 10% to greater than 95%, a way of controlling the variation in the reaction temperature in the catalytic gas-phase oxidation of methacrolein to methacrylic acid in a fixed-bed reactor with contacting tubes in such a manner that the contacting tubes are surrounded by a salt melt at 330° or 340° C. However, this process has the disadvantage that the variations in reaction temperature which are set implicitly along the contact tubes are not entirely satisfactory with respect to highly selective conversion of methacrolein to methacrylic acid, in particular in the conversion range of from 40 to 95% of reacted methacrolein (for a single pass).

It is an object of the present invention to provide a process for the catalytic gas-phase oxidation of methacrolein to methacrylic acid in a fixed-bed reactor having contacting tubes, at elevated temperature on catalytically active oxides with a conversion of methacrolein for a single pass of from 40 to 95%, which has a reaction temperature program which is improved with respect to increased selectivity of formation of methacrylic acid.

We have found that this object is achieved by a process for the catalytic gas-phase oxidation of methacrolein to methacrylic acid in a fixed-bed reactor with contacting tubes, at elevated temperature on catalytically active oxides with a conversion of methacrolein for a single pass of from 45 to 95%, wherein the reaction temperature in the flow direction along the contacting tubes (along the reaction axis) in a first reaction zone from entry of the starting reaction gases containing the reactants into the contacting tubes is from 280° to 340° C. until a methacrolein conversion of from 20 to 40% is reached, and the reaction temperature is subsequently reduced by a total of from 5° to 40° C., abruptly or successively in steps or continuously along the contacting tubes until a methacrolein conversion of from 45 to 95% has been reached, with the proviso that the reaction temperature in this second reaction zone is not lower than 260° C.

Suitable oxidic catalysts are, inter alia, the materials described in EP-A 265 733, EP-A 102 688 and DE-A 3 010 434.

Preference is given to materials of the formula $$Mo_{12}P_aX_b^1X_c^2X_d^3X_f^5O_n \qquad (I),$$

where
 $X^1$ is at least one alkali metal and/or alkaline earth metal,
 $X^2$ is arsenic, tungsten, niobium and/or vanadium,
 $X^3$ is antimony, bismuth, zirconium and/or boron,
 $X^4$ is chromium, cobalt, manganese, tin, sulfur, zinc, silicon, selenium, iron and/or nickel,
 $X^5$ is copper, silver, rhodium and/or rhenium,
 a is from 0.3 to 3,
 b is from 0 to 3,
 c is from 0 to 3,
 d is from 0 to 3,
 e is from 0 to 3,
 f is from 0 to 2 and
 n is a number determined by the valency and frequency of the elements other than oxygen in the formula I.

Particular preference is given to materials of the formula II $$Mo_{12}P_aV_bX_c^1X_d^2X_e^3Sb_fRe_gS_hO_n \qquad (II)$$

where
 $X^1$ is potassium, rubidium and/or cesium,
 $X^2$ is copper and/or silver
 $X^3$ is cerium, boron, zirconium, manganese and/or bismuth,
 a is from 0.5 to 3.0,
 b is from 0.01 to 3.0,
 c is from 0.2 to 3.0,
 d is from 0.01 to 2.0,
 e is from 0 to 2.0,
 f is from 0.01 to 2.0,
 g is from 0 to 1.0,
 h is from 0.001 to 0.5 and
 n is a number determined by the valency and frequency of the elements other than oxygen in the formula II, where particularly preferred materials of the formula II are those having the composition $$Mo_{12}P_2V_1Cs_2K_{0.03}Cu_{0.5}Sb_1S_{0.03}Re_{0.04}.$$

Said oxidic catalysts can be obtained in a conventional manner. They can be prepared, for example, by finely distributing, as starting compounds, suitable salts of the elemental constituents which make up the catalysts, if desired at elevated temperature and with addition of acids or bases, in an aqueous medium by dissolution and/or suspension, mixing the solutions or suspensions, drying the mixture, shaping the resultant material and calcining the product in a stream of air or in an inert atmosphere, for example $N_2$ or $CO_2$, in general at from 180° to 480° C., preferably from 350° to 450° C. During shaping, conventional assistants such as lubricants (e.g. graphite) or shaping aids and reinforcing agents, such as glass, asbestos, silicon carbide or potassium titanate microfibers, can be added. In this form, the oxidic materials are expediently prepared for use as unsupported catalysts, the preferred catalyst geometry being hollow cylinders having an external diameter and length of from 4 to 10 mm and a wall thickness of from 1 to 3 mm. Further details are given in the earlier German Patent Application 4 022 212.8. However, the catalytically active oxides may also be used in the form of shell catalysts, ie. on a preshaped carrier material, it being possible for the oxides to be applied to the carrier material, for example, in the form of an aqueous starting solution or suspension, together with subsequent drying and calcination, or as a pre-calcined, powdered material in combination with a binder.

It is of course also possible for the catalytically active oxidic materials to be employed in powder form as catalysts.

The oxygen required for the oxidation of the methacrolein can be supplied, for example, in the form of air, but also in pure form. Due to the high heat of reaction, the reactants are preferably diluted with an inert gas such as $N_2$, recovered reaction offgases and/or steam. In general, the oxidation is carried out at a methacrolein:oxygen:steam:inert gas volume (l(s.t.p.)) ratio of from 1:(1 to 3):(2 to 20):(3 to 30), preferably from 1:(1 to 3):(3 to 10):(7 to 18). The reaction pressure is generally from 1 to 3 bar and the total space velocity is preferably from 800 to 1800 l(s.t.p.)/l/h. It is advantageous in the process according to the invention to employ methacrolein, which is obtainable in a known manner by condensing propanol with formaldehyde in the presence of secondary amines and acids in the liquid phase. In the process described, pure methacrylic acid is not obtained; instead, a gas mixture from whose secondary components methacrylic acid can be removed in a known manner, is obtained.

The reaction temperature profile according to the invention can be achieved in a manner known per se, for example by zone heating or cooling of the contacting tubes by means of electrical heating bands or circulating heating fluids, such as melts of salts such as potassium nitrate, sodium nitrite and/or sodium nitrate, or of low-melting metals, such as sodium, tin, mercury and alloys of various metals, or heat-transfer oils; if there is only a single tube, the high heat transfer means that the temperature prevailing inside the tube during the reaction is essentially equal to the external heating or cooling temperature.

However, zone heating or cooling is also possible in multiple-tube fixed-bed reactors, as preferably employed for large-scale industrial implementation of the process according to the invention and described, for example, in DE-A 2 830 765, DE-A 2 201 528, DE-A 1 601 162, DE-A 2 513 405 and US-A 3,147,084. Another way of controlling the reaction temperature is to increase or reduce the catalyst activity in zones. This can be done by chemically modifying the active catalyst material or by dilution with deactivated catalyst or inert material. Zone heating/cooling may also be combined with increasing/reducing the catalyst activity in zones. Particularly favorable selectivities are achieved if a methacrolein conversion of from 50 to 75% is used. It is particularly advantageous to reduce the reaction temperature by a total of from 10° to 40° C. after the first reaction zone, either abruptly or successively in steps or continuously along the reaction axis until the final methacrolein conversion has been reached. A stepwise reduction is preferred for technical reasons, generally in from 2 to 4 steps.

Since only finite heat transfer from the heating medium to the reaction gases can be achieved when working on an industrial scale, in particular if a multiple-tube fixed-bed reactor heated by means of a salt bath is used, it has proven advantageous to feed the starting reaction gases to the first reaction zone after preheating, generally to the reaction temperature. If a temperature of the heating medium of above 280° C., but $\leq 310°$ C., is selected along the first reaction zone, the reaction gases are preferably fed to the first reaction zone after preheating to a temperature from 20° to 30° C. above the temperature of the heating medium at the beginning of the first reaction zone. If the temperature of the heating medium along the first reaction zone is in the range from 310° to not more than 340° C., the reaction gases are preferably fed to the first reaction zone after preheating to a temperature only up to 15° C. above the temperature of the heating medium at the beginning of the first reaction zone. If the temperature of the heating medium along the first reaction zone is constant, a continuously falling reaction temperature is established in the flow direction along the first reaction zone. This has proven particularly advantageous, in particular if the continuous drop in reaction temperature is continued in the flow direction along the second reaction zone. It is of course possible for the continuous drop in reaction temperature along the reaction axis to be approximated by successive stepwise drops in temperature. The drop in reaction temperature along the first reaction zone in the flow direction is preferably from 5° to 40° C., particularly preferably from 15° to 40° C.

Typical contacting tubes comprise corrosion- and heat-resistant steel (e.g. V2A), and have a wall thickness of about 2 mm and an internal diameter of 25 mm. The number of these tubes in a multiple-tube fixed-bed reactor is generally from 10,000 to 40,000. The conversion U and selectivity S are defined as follows in this document:

$$U = \frac{\text{number of moles of methacrolein reacted}}{\text{number of moles of methacrolein employed}} \times 100$$

$$S = \frac{\text{number of moles of methacrylic acid formed}}{\text{number of moles of methacrolein reacted}} \times 100$$

EXAMPLES B1 TO B4 AND COMPARATIVE EXAMPLES V1 TO V2

A steel tube (V2A, wall thickness 2 mm, internal diameter 25 mm) zone-heated by means of electrical heating bands was filled to a level of 3 m with an unsupported catalyst as described in Example 1 of the earlier German Patent Application 4 022 212.82 and charged with 1200 l(s.t.p.)/l/h of a gas mixture having the composition 4.5% by volume of methacrolein,
9.5% by volume of oxygen,
24 % by volume of steam and
62 % by volume of nitrogen, which was preheated to various temperatures $T^1$ depending on the example. The temperature of the electrical heating bands was subsequently adjusted to $T^2$ along the first reaction zone to a methacrolein conversion of 40% and then to $T^3$ until the reaction gases left the tube. The end conversion $U_{end}$ was determined by the length of the second reaction zone. The results obtained (selectivity $S_{end}$ of the methacrylic acid formation) are shown in the table.

TABLE

|    | $T^1$ | $T^2$ | $T^3$ | $U_{end}$ | $S_{end}$ |
|----|-------|-------|-------|-----------|-----------|
| B1 | 300   | 300   | 286   | 69        | 87.3      |
| B2 | 310   | 310   | 281   | 70        | 88.5      |
| B3 | 320   | 320   | 278   | 69        | 87.0      |
| B4 | 330   | 310   | 279   | 70        | 88.7      |
| V1 | 290   | 290   | 290   | 68        | 85.4      |
| V2 | 270   | 270   | 328   | 69        | 81.3      |

We claim:

1. A process for the catalytic gas-phase oxidation of methacrolein to methacrylic acid in a fixed-bed reactor with contacting tubes, at elevated temperature on catalytically active oxides with a conversion of methacrolein for a single pass of from 40 to 95 mol%, wherein the reaction temperature in the flow direction along the contacting tubes in a first reaction zone from entry of the starting reaction gases containing the reactants into the contacting tubes is from 280° to 340° C. until a methacrolein conversion of from 20 to 40% is reached, and the reaction temperature is subsequently reduced by a total of from 5° to 45° C., abruptly or successively in steps or continuously along the contacting tubes until a methacrolein conversion of from 45 to 95% has been reached, with the proviso that the reaction temperature in this second reaction zone is not lower than 260° C.

2. A process as claimed in claim 1, wherein the reaction temperature of the reaction gases drops successively in the flow direction along the contacting tubes until they leave the contacting tubes.

3. A process as claimed in claim 1, wherein the oxidic catalysts are materials of the formula I $$Mo_{12}P_aX_b^1X_c^2X_d^3X_e^4X_f^5O_n \qquad (I).$$

where
- $X^1$ is at least one alkali metal and/or alkaline earth metal,
- $X^2$ is arsenic, tungsten, niobium and/or vanadium,
- $X^3$ is antimony, bismuth, zirconium and/or boron,
- $X^4$ is chromium, cobalt, manganese, tin, sulfur, zinc, silicon, selenium, iron and/or nickel,
- $X^5$ is copper, silver, rhodium and/or rhenium,
- a is from 0.3 to 3,
- b is from 0 to 3,
- c is from 0 to 3,
- d is from 0 to 3,
- e is from 0 to 3,
- f is from 0 to 2 and
- n is a number determined by the valency and frequency of the elements other than oxygen in the formula I.

4. A process as claimed in claim 1, wherein the oxidic catalysts are materials of the formula II $$Mo_{12}P_aV_bX_c^1X_d^2X_e^3Sb_fRe_gS_hO_n \qquad (II)$$

where
- $X^1$ is potassium, rubidium and/or cesium,
- $X^2$ is copper and/or silver
- $X^3$ is cerium, boron, zirconium, manganese and/or bismuth,
- a is from 0.5 to 3.0,
- b is from 0.01 to 3.0,
- c is from 0.2 to 3.0,
- d is from 0.01 to 2.0,
- e is from 0 to 2.0,
- f is from 0.01 to 2.0,
- g is from 0 to 1.0,
- h is from 0.001 to 0.5 and
- n is a number determined by the valency and frequency of the elements other than oxygen in the formula II.

* * * * *